United States Patent [19]

Ito et al.

[11] Patent Number: 4,956,471

[45] Date of Patent: Sep. 11, 1990

[54] PROCESS FOR ISOLATING AND PURIFYING AMINO ACIDS

[75] Inventors: Hisao Ito; Akio Nishi; Masasi Miyazawa; Masayoshi Naruse, all of Kawasaki, Japan

[73] Assignee: Ajinomoto Company, Inc., Tokyo, Japan

[21] Appl. No.: 355,821

[22] Filed: May 16, 1989

Related U.S. Application Data

[63] Continuation of Ser. No. 238,529, Aug. 31, 1988, abandoned.

[30] Foreign Application Priority Data

| Apr. 28, 1986 | [JP] | Japan | 61-98512 |
| Apr. 28, 1986 | [JP] | Japan | 61-98513 |
| May 23, 1986 | [JP] | Japan | 61-118867 |
| Jun. 11, 1986 | [JP] | Japan | 61-135517 |
| Jun. 20, 1986 | [JP] | Japan | 61-144260 |

[51] Int. Cl.$^5$ .................... C07D 233/64; C07C 99/12
[52] U.S. Cl. .................................... 548/344; 562/554
[58] Field of Search ........................ 562/554; 548/344

[56] References Cited

U.S. PATENT DOCUMENTS

| 2,684,331 | 7/1954 | Bauman | 210/672 |
| 2,771,193 | 11/1956 | Simpson | 210/672 |
| 4,133,753 | 1/1979 | Takeuchi et al. | 562/516 |

FOREIGN PATENT DOCUMENTS

| 6208 | 3/1965 | Japan | 562/554 |
| 1055 | 1/1970 | Japan | 562/554 |
| 131550 | 10/1981 | Japan | 562/554 |

OTHER PUBLICATIONS

*Chem. Eng. Progress*, 52, p. 430 Oct. 1956, Wheaton et al.
Helftman, E., *Chromatography*, 2nd Edition, 1967, pp. 295-297.
Helfferich, F., *Ion Exchange*, 1962, pp. 134, 135, 430-433.
Asher, D. R., Glycerol Purification by Ion Exclusion, 1956, pp. 518-521.
Wheaton, R. M. and Bauman, W. C., Ion Exclusion, *Industrial and Engineering Chemistry*, 1953, pp. 228-233.
Simpson, D. W. and Bauman, W. C., Concentration Effects of Recycling in Ion Exclusion, *Industrial and Engineering Chemistry*, 1954, pp. 1958-1963.
Applebaum, S. B., *Demineralization by Ion Exchange*, Academic Press, New York, 1968, pp. 368,369,374,375.
Fellicetta, V. F. et al., Spent Sulfite Liquor VII, *TAPPI* 1959, pp. VII, 1959, pp. 496-502.
Asher, D. R., Sugar Purification by Ion Exclusion, 1956, *Industrial and Engineering Chemistry* pp. 1465-1467.
Seamster, A. H. and Wheaton, R. M., Ion Exchange Becomes Powerful Processing Tool, *Chemical Engineering* 1960, pp. 115-120.
Wheaton, R. M., New Uses for Ion Exchange Resins, 1956, *Chemical Engineering Progress* pp. 428-432.

*Primary Examiner*—Bruce Gray
*Attorney, Agent, or Firm*—Oblon, Spivak, McClelland, Maier & Neustadt

[57] ABSTRACT

A process for isolating and purifying an amino acid, which comprises subjecting an aqueous solution of said amino acid containing impurities composed mainly of at least one member selected from the group consisting of acidic amino acids, lysine, ornithine, citrulline, histidine, PCA, sulfate ions, chloride ions and pigments to ion-exclusion chromatography using a strongly acidic cation exchange resin.

5 Claims, No Drawings

PROCESS FOR ISOLATING AND PURIFYING AMINO ACIDS

This application is a continuation of 07/238,529 filed 08/31/88, which is a continuation of 07/038,064 filed 4/14/87 both now abandoned.

BACKGROUND OF THE INVENTION

1. Field of the Invention

The present invention relates to a process for isolating and purifying amino acids.

2. Description of the Related Art

Amino acids are usually produced by fermentation processes using, for example, glucose as a main starting material. The fermentation liquor obtained by such method contains, as impurities, several kinds of by-product amino acids, as well as sulfate ions, chloride ions, and pigments. This type of fermentation liquor is a typical amino acid solution which may be used according to the process of the present invention. In addition, aqueous amino acid solutions obtained by other methods may also be treated by the process of this invention.

Various processes for isolating and purifying amino acids from their fermentation liquors are known. Examples of these processes involving various amino acids will now be discussed.

Histidine may be isolated and purified from its fermentation liquor by repeated crystallization; adsorption of histidine on a strongly acidic cation-exchange resin to remove the impurities followed by elution of adsorbed histidine with a suitable eluant such as ammonia; and addition of an inorganic acid to increase adsorption [Japanese Patent Kokai No. 148094 (1976)].

Valine may be isolated and purified from a valine fermentation liquor by repeated crystallization; a specific fractional crystallization process for solutions of valine containing leucine and isoleucine which are similar in structure to valine [Japanese Patent Kokai No. 16450 (1981)]; and adsorption of valine on a strongly acidic cation-exchange resin to remove the impurities involved, followed by elution of adsorbed valine.

Processes for purifying threonine from its fermentation liquor include repeated crystallization; and adsorption of threonine on a strongly acidic cation-exchange resin to remove the impurities involved, followed by elution of adsorbed threonine with a suitable eluant such as ammonia [Japanese Patent Kokai Nos. 77090 (1973), 32693 (1979)].

Methods for isolating and purifying isoleucine from isoleucine fermentation liquors include repeated crystallization [Process for Purifying Hydrochlorides, Japanese Patent Kokai No. 62554 (1984)]; a specific fractional crystallization process for solutions of isoleucine containing leucine and valine which are similar in structure to isoleucine [Japanese Patent Kokai Nos. 16450 (1981), 123622 (1975)]; and adsorption of isoleucine on a strongly acidic cation-exchange resin to remove the impurities involved, followed by elution of adsorbed isoleucine [Japanese Patent Kokai Nos. 126878 (1975), 131550 (1981)].

A method has been proposed for isolating and purifying arginine from an arginine fermentation liquor [Japanese Patent Kokai No. 6778 (1975)], in which said fermentation liquor is brought into contact with a strongly acidic cation-exchange resin to adsorb arginine, followed by elution of adsorbed arginine with an aqueous solution of ammonia and ammonium chloride. In this case, microbial cells and a portion of the pigments are removed during the adsorption process.

The processes which have been proposed for isolating and purifying glutamine from glutamine fermentation liquors include (1) use of an OH-type anion-exchange resin to fix the impurities involved at the isoelectric point of glutamine, thereby recovering a solution of pure glutamine as effluent; or converting glutamine into a cation at a low pH, allowing the cationic glutamine thus formed to be adsorbed on a strongly acidic cation-exchange resin, then washing off unadsorbed impurities and finally eluting the adsorbed glutamine (in these processes, microbial cells and pigments are removed before or after the chromatographic opera ion) [Japanese Patent Kokai Nos. 81587 (1974), 89590 (1975), 3040 (1981)]; and (2) repeated crystallization [Japanese Patent Kokai No. 95481 (1975)].

Generally speaking, the above-mentioned crystallization processes have the disadvantage of low product yields because of the repetition of the crystallization steps. The methods involving adsorption of an amino acid on a strongly acidic cation-exchange resin to remove the impurities followed by elution of adsorbed amino acid have a problem in that such methods involve fluctuations in the pH of the system which tend to cause the amino acid to pass unadsorbed through the resin, thus resulting in low product yield.

In the case of glutamine, the ion exchange processes have the disadvantages that during the fluctuations in pH, glutamine undergoes ion exchange with the resin or passes through the resin unadsorbed, thus leading to a loss in product yield. Another disadvantage is that glutamine tends to be decomposed into glutamic acid and PCA ["Chemistry of the Amino Acids", page 1933 (1961), John Wiley and Sons, Inc.].

The processes involving the use of cation-exchange resins are further disadvantageous in that they also call for the use of acids and alkalis to reactivate the resin, and complex operation. Moreover, in the case of, for example, arginine, pure arginine cannot be isolated because by-product amino acids such as lysine, ornithine, citrulline and histidine, behave similarly to arginine under these conditions.

In spite of the above-described known methods, there is a continuing need for new and improved methods for purifying amino acids from solutions thereof.

SUMMARY OF THE INVENTION

Accordingly, it is an object of the present invention to provide a process for purifying an amino acid from a solution thereof.

It is yet another object of the present invention to isolate a highly pure amino acid from an aqueous solution thereof containing various impurities.

These and other objects of the invention as will hereinafter become more readily apparent have been accomplished by providing a method for isolating high purity amino acids from solutions thereof containing impurities, which method comprises subjecting the amino-acid containing solution to ion-exclusion chromatography using a strongly acidic cation-exchange resin.

DETAILED DESCRIPTION OF THE PREFERRED EMBODIMENTS

This invention relates to a process for isolating and purifying amino acids. More particularly, it relates to a process for isolating a high purity amino acid from an aqueous solution thereof containing impurities. Preferred amino acids which may be purified by the process of this invention include histidine, isoleucine, threonine, glutamine, arginine, and valine. However, other amino acids, such as other members of the 20 naturally occurring amino acids, could be purified by this method. Impurities involved in the cases of, for example, isoleucine, threonine, valine, and histidine are composed mainly of at least one member selected from acidic amino acids, sulfate ions, chloride ions and pigments. In the case of arginine, the impurities are composed mainly of at least one member selected from lysine, ornithine, citrulline, histidine, sulfate ions, chloride ions, and pigments. In the case of glutamine, the impurities are composed mainly of at least one member selected from the group consisting of glutamic acid, pyrrolidone carboxylic acid (PCA for short), and sulfate ions. The present method comprises subjecting the impure aqueous solution of an amino acid to ion-exclusion chromatography using a strongly acidic cation-exchange resin.

The inventors have discovered that high-purity amino acid can be recovered with a high yield by introducing the ion-exclusion chromatography step into a process for isolating amino acid. The invention was accomplished based on such findings.

Nonelectrolytes and weak electrolytes can generally be separated from strong electrolytes by ion-exclusion chromatography. This is because the Donnan potential formed by the electrically charged ion-exchange groups excludes strong-electrolyte molecules, thus preventing them from penetrating into the ion-exchange resin, whereas nonelectrolytes and weak electrolytes can freely penetrate into the resin. This principle is generally involved in the present invention.

By an aqueous solution of an amino acid containing impurities as used in the present specification, is meant amino acid fermentation liquors containing microbial cells or those which have the microbial cells removed, solutions of crude amino acid obtained from such fermentation liquors, mother liquors of crystallized amino acid, and the like. In general, any aqueous solution of an amino acid containing impurities composed mainly of at least one member selected from the group consisting of acidic amino acids, sulfate ions, chloride ions and pigments may be used for the process of this invention. When arginine is the amino acid to be purified, the aqueous solution thereof may contain impurities composed mainly of at least one member selected from lysine, ornithine, citrulline, histidine, sulfate ions, chloride ions, and pigments. When glutamine is the amino acid to be purified, the aqueous solution thereof may contain impurities composed mainly of at least one member selected from glutamic acid, pyrrolidone carboxylic acid, and sulfate ions. By acidic amino acids is meant, for example, aspartic acid, glutamic acid, and the like. There is no specific limitation upon the concentration of the amino acid so long as the amino acid is completely in solution.

Before subjecting the aqueous solution of the amino acid containing impurities to ion-exclusion chromatography, the pH thereof should be adjusted to the isoelectric point of the amino acid or to a pH level in the vicinity thereof, thereby bringing most of the amino acid molecules into a neutral (uncharged) state. Acidic amino acids, sulfate ions and chloride ions are present as anions under this condition. At the isoelectric point of arginine, or a pH in the vicinity thereof, the impurities in the arginine fermentation liquor such as lysine, ornithine, citrulline, histidine, sulfate ions and chloride ions are present as anions. At the isoelectric pH of glutamine, or a pH in the vicinity thereof, glutamic acid, PCA, and sulfate ions are present as anions.

A preferred pH range is the isoelectric point $\pm 1$ pH units, more preferably the isoelectric point $\pm 0.5$ pH units, and most preferably the isoelectric point $\pm 0.2$ pH units. For arginine, the isoelectric point is 11.15, for histidine 7.47, for valine 5.96, for threonine 5.64, and for isoleucine, 5.94, and for glutamine, 5.65.

The strongly acidic cation-exchange resin, on the other hand, should be in a cationic form, with a cation that is the counter-ion of the above-mentioned anions. For example, the acidic amino acids, PCA, sulfate ions, and chloride ions are generally present in the form of ammonium salts in amino acid fermentation liquors; hence, the strongly acidic cation-exchange resin should be used in the form of an ammonium salt in such a case.

In ion-exclusion chromatography, the separation efficiency tends to be lower when the system contains several kinds of cations. To avoid this, it is preferable that the aqueous solution be pretreated with, for example, a cation exchange resin to remove the impurity cations. Ion exclusion chromatography can also be effected by the use of an anion exchange resin. In the case of purification of histidine, valine, threonine, and isoleucine, however, the use of an anion-exchange resin is unsuitable, because acidic amino acids, sulfate ions and chloride ions are all present in the form of anions at the isoelectric point of the particular amino acid and this tends to lower the separation efficiency. Similarly, in the case of purification of arginine, the use of an anion exchange resin is unsuitable because lysine, ornithine, citrulline, histidine, sulfate ions and chloride ions are all present in the form of anions at the isoelectric point of arginine and this tends to lower separation efficiency. Further, in the case of glutamine, the use of anion exchange resin is unsuitable because glutamic acid, PCA, and sulfate ions are all present in the form of anions at the isoelectric point of glutamine lowering the separation efficiency.

Typical examples of the strongly acidic cation-exchange resin used in the process of this invention include Diaion SK-102, SK-104, SK-106, SKIB, SK-104S, SKIBS and UBK-101L (Mitsubishi Chemical Industries); XFS-43279, XFS-43280, XFS-43281, HCR-W2 and TG-8500A (Dow Chemical); C-20 (aryl sulfonic cross-linked polystyrene), C-25D, ES-26 and C-3 (Amberlite IR) (Duolyte); S-100, S-109, SP-112 and Sp-120 (Revacit); IR-116, IR-118, IR-120B, IR-122, IR-124, IR-252, IR-200 and IR-200CT (Amberlite; phenolic methylene sulfonic). Of these, the highest separation efficiency can be expected from those resins whose crosslinking degree is 4 to 8%.

According to the invention, a suitable amount of the strongly acidic cation-exchange resin to be used is approximately four to five times as much as the amount of aqueous amino acid solution when the solution contains, e.g., about 2% of histidine and about 0.5% of impurities; about 7% of valine and about 3% of impurities; about 6% of threonine and about 2% of impurities; about 3% of isoleucine and about 2% of impurities; about 10% of arginine and about 1% of impurities; and about 6% of glutamine and about 1% of impurities. Lesser amounts of the resin may suffice for solutions of lower amino acid and impurity concentrations. Those of ordinary skill in the art will readily be able to determine the optimum amount of resin to be used by preliminary experiments.

There is no specific limitation upon the treating temperature so long as it is within the allowable working temperature of the resin used. The higher the treating temperature, the higher the separation speed of amino acid from impurities.

A column is packed with a strongly acidic cation exchange resin in the form corresponding to the cations contained in the solution to be treated, and a suitable amount of the solution is added to the top of the column. When an amino acid fermentation liquor is used, for example, a column is packed with a strongly acidic cation exchange resin in the form of an ammonium salt, and the fermentation liquor, with its pH previously adjusted to the isoelectric point of the amino acid or to a pH level in the vicinity thereof, is poured onto the column. Introducing water into the column will first elute the impurities contained, followed by elution of the amino acid. In the case of arginine, a column is packed with a strongly acidic cation-exchange resin in the form of a sodium salt, and fermentation liquor, with its pH previously adjusted to the isoelectric point of arginine or to a pH level in the vicinity thereof, is poured onto the column. Introducing water through the column as an eluant will first elute the impurities involved, followed by elution of arginine. During elution of arginine, however, ion exchange takes place between the resin and a small amount of arginine present as cations (Example 7). The inventors have found that this disadvantage can be avoided if a caustic soda solution whose pH is at the isoelectric point of arginine or higher is used as eluant in place of pure water. Arginine can thus be recovered at a rate of nearly 100% without being left adsorbed on the resin. (Example 8).

If microbial cells and/or pigments are contained in the amino acid fermentation liquor which is subjected to ion-exclusion chromatography, there is usually no problem presented because these behave in the same manner as ammonium salts of acidic amino acids, sulfate ions and chloride ions. However, microbial cells may be previously removed from the fermentation liquor as required, to prevent possible clogging of the resin layer in the column.

Similarly, the microbial cells and/or pigments, if contained in the arginine fermentation liquor to be subjected to ion-exclusion chromatography, usually offer no problem because these behave in the same manner as sodium salts of lysine, ornithine, citrulline, histidine, sulfate ions and chloride ions. Further, microbial cells and/or pigments, if contained in the glutamine fermentation liquor to be subjected to ion-exclusion chromatography, usually offer no problem because these behave in the same manner as ammonium salts of glutamic acid, PCA and sulfate ions.

There is no specific limitation on the flow rate of water (SV) through the column, and a commonly used SV level of about 0.5 to 4 may be adopted. The fractions containing pure amino acid can be collected by tracing the changes in pH and refractive index of the eluate. Known techniques may be used to recover the purified amino acid from the collected fractions.

The invention now being generally described, the same will be better understood by reference to certain specific examples which are included herein for purposes of illustration only and are not intended to be limiting of the invention or any embodiment thereof, unless specified.

EXAMPLES

Example 1

Forty-eight milliliters of an aqueous solution containing 20 g/l L-histidine, 5 g/l ammonium glutamate, 0.1 g/l ammonium sulfate and 3 g/l ammonium chloride, obtained by removal of microbial cells from L-histidine fermentation liquor, were added to the top of a column ($\phi$3 cm×H30 cm) packed with 212 ml of $NH_4$-type XFS-43279 (degree of crosslinking: 4%), and water was then introduced at 60° C., at a pH of 7.15 and at an SV of 1.7 to effect elution.

Ammonium glutamate, ammonium sulfate and ammonium chloride were first eluted, followed by elution of L-histidine. The part of the eluate ranging from 80 ml to 350 ml output was collected, and was divided into the primary fraction (170 ml–350 ml output) and the secondary fraction (80 ml–160 ml output).

The primary fraction contained L-histidine as major component, the removal efficiency for ammonium glutamate, ammonium sulfate and ammonium chloride being 97%, 92% and 97%, respectively, and the L-histidine recovery rate being 99.9%. The color value of original histidine solution was 3.49 (as measured with a spectrophotometer at 400 nm), while that of the primary fraction was 0.430 on average, the decolorization degree being 73%.

Example 2

Forty-eight milliliters of an aqueous solution containing 20 g/l L-histidine, 5 g/l ammonium glutamate, 0.08 g/l ammonium sulfate and 2 g/l ammonium chloride, obtained by removal of microbial cells from L-histidine fermentation liquor, were added to the top of a column ($\phi$3 cm×H30 cm) packed with 212 ml of $NH_4$-type XFS-43279 (degree of crosslinking: 4%), and water was then introduced at 60° C., at a pH of 7.50 and at an SV of 1.1 to effect elution.

Ammonium glutamate, ammonium sulfate and ammonium chloride were first eluted, followed by elution of L-histidine. The part of the eluate ranging from 80 ml to 350 ml output was collected, and was divided into the primary fraction (170 ml–350 ml output) and the secondary fraction (80 ml–160 ml output).

The primary fraction contained L-histidine as major component, the removal efficiency for ammonium glutamate, ammonium sulfate and ammonium chloride being 98%, 97% and 99%, respectively, and the L-histidine recovery state being 99%. The color value of original histidine solution was 3.32 (as measured with a spectrophotometer at 400 nm), while that of the primary fraction was 0.228 on average, the decolorization degree being 84%.

Example 3

Forty-eight milliliters of an aqueous solution containing 29 g/l isoleucine, 2 g/l ammonium glutamate, 10 g/l ammonium sulfate and 9 g/l ammonium chloride, obtained by removal of microbial cells from isoleucine fermentation liquor, were added to the top of a column ($\phi$3.2 cm×H25 cm) packed with 200 ml of $NH_4$-type XFS-43279 (degree of crosslinking: 4%), and water was then introduced at 60° C., at a pH of 5.96 and at an SV of 1.0 to effect elution.

Ammonium glutamate, ammonium sulfate and ammonium chloride were first eluted, followed by elution of isoleucine. The part of the eluate ranging from 80 ml to 350 ml output was collected, and was divided into the primary fraction (170 ml–350 ml output) and the secondary fraction (80 ml–160 ml output). The primary fraction contained isoleucine as the major component, the removal efficiency for ammonium glutamate, ammonium sulfate and ammonium chloride being 100.0%, 98.3% and 97.29%, respectively, and the isoleucine recovery rate being 99.9%. The color value of the original isoleucine solution was 1.79 (as measured with a spectrophotometer at 400 nm), while that of the primary fraction was 0.113 on average, the degree of decolorization being 75.6%.

Example 4

Forty-eight milliliters of an aqueous solution containing 60 g/l L-valine, 2 g/l ammonium glutamate, 15 g/l ammonium sulfate and 15 g/l ammonium chloride, obtained by removal of microbial cells from L-valine fermentation liquor, were added to the top of a column ($\phi$3.2 cm×H25 cm) packed with 200 ml of NH$_4$-type XFS43279 (degree of crosslinking: 4%), and water was then introduced at 45° C., at a pH of 5.96 and at an SV of 1.0 to effect elution.

Ammonium glutamate, ammonium sulfate and ammonium chloride were first eluted, followed by elution of L-valine. The part of the eluate ranging from 80 ml to 350 ml output was collected, and was divided into the primary fraction (170 ml–350 ml output) and the secondary fraction (80 ml–160 ml output). The primary fraction contained L-valine as the major component, the removal efficiency for ammonium glutamate, ammonium sulfate and ammonium chloride being 91%, 93% and 89%, respectively, and the L-valine recovery rate being 99%. The color value of the original valine solution was 2.38 (as measured with a spectrophotometer at 400 nm), while that of the primary fraction was 0.108 on average, the degree of decolorization being 78%.

Example 5

Twenty milliliters of an aqueous solution containing 50 g/l L-valine and 10 g/l ammonium sulfate were added to the top of a column (L/D = 12) packed with 100 ml of NH$_4$-type SK104S (degree of crosslinking: 4%), and water was then introduced at 60° C., at a pH of 9.0 and at an SV of 1.5 to effect elution.

Ammonium sulfate was first eluted, followed by elution of L-valine. The part of the eluate ranging from 60 ml to 150 ml output was collected, and was divided into the primary fraction (110 ml–150 ml output) and the secondary fraction (60 ml–100 ml output). The primary fraction contained L-valine as the major component, the removal efficiency for ammonium sulfate being 96.0% and the L-valine recovery rate being 99.0%.

Example 6

Forty milliliters of an aqueous solution containing 60 g/l threonine, 0.6 g/l ammonium glutamate, 4 g/l ammonium sulfate and 13 g/l ammonium chloride, (pH =5.64), obtained by removal of microbial cells from L-threonine fermentation liquor, were added to the top of a column ($\phi$3.2 cm×H25 cm) packed with 200 ml of NH$_4$-type XFS-43279 (degree of crosslinking: 4%), and water was then introduced at 45° C., at an SV of 1.0 to effect elution.

Ammonium glutamate, ammonium sulfate and ammonium chloride were first eluted, followed by elution of L-threonine. The part of the eluate ranging from 80 ml to 350 ml output was collected, and was divided into the primary fraction (160 ml–310 ml output) and the secondary fraction (80 ml–150 ml output). The primary fraction contained L threonine as the major component, the removal efficiency for ammonium glutamate, ammonium sulfate and ammonium chloride being 93%, 82% and 89%, respectively, and the L-threonine recovery rate being 97%. The color value of the original threonine solution was 2.828 (as measured with a spectrophotometer at 400 nm), while that of the primary fraction was 0.109 on average, the degree of decolorization being 84.5%.

Example 7

Forty milliliters of an aqueous solution containing 100 g/l L-arginine, 10 g/l lysine sodium salt (pH =11.3) were added to the top of a column ($\phi$3.2 cm×H25 cm) packed with 200 ml of Na-type XFS-43279 (degree of crosslinking: 4%), and water was then introduced at 45° C., at an SV of 1.0 to effect elution.

Lysine sodium salt was first eluted, followed by elution of L-arginine. The part of the eluate ranging from 80 ml to 360 ml output was collected, and was divided into the primary fraction (170 ml–360 ml output) and the secondary fraction (80 ml–160 ml output). The primary fraction contained L-arginine, with lysine sodium salt being completed removed. The L-arginine recovery rate was 70%, and all the lysine sodium salt was recovered in the second fraction (recovery rate: 100%). pH Measurement showed that it tends to be lower in the primary fraction, suggesting that part of arginine was present as a cation and was left adsorbed on the resin.

As can be seen from this example, mutual separation between arginine and lysine also forms a part of this invention.

Example 8

Forty milliliters of an aqueous solution containing 100 g/l L-arginine, 10 g/l lysine sodium salt (pH = 12.0) were added to the top of a column ($\phi$3.2 cm×H25 cm) packed with 200 ml of Na-type XFS-43279 and an aqueous caustic soda solution with a pH of about 13 was then introduced at 45° C., at an SV of 1.0 to effect elution.

Lysine sodium salt was first eluted, followed by elution of L-arginine. The par of the eluate ranging from 80 ml to 360 ml output was collected, and was divided into the primary fraction (170 ml–360 ml output) and the secondary fraction (80 ml–160 ml output). The primary fraction contained only L-arginine, with lysine sodium salt being completed removed. The L-arginine recovery rate was 99%.

Example 9

Forty milliliters of an aqueous solution containing 80 g/l L-arginine, 4 g/l lysine sodium salt, 3 g/l ornithine sodium salt, 8 g/l citrulline sodium salt, 0.4 g/l histidine sodium salt, 8.5 g/l sodium chloride and 0.3 g/l sodium sulfate (pH=11.32), obtained by removal of microbial cells from L-arginine fermentation liquor, were added to the top of a column ($\phi$3.2 cm×H25 cm) packed with 200 ml of Na-type XFS-43279 and an aqueous caustic soda solution with a pH of about 13 was then introduced at 45° C. at an SV of 1.0 to effect elution.

Lysine sodium salt, ornithine sodium salt, citrulline sodium salt, histidine sodium salt, sodium chloride and sodium sulfate were first eluted, followed by elution of L-arginine. The part of the eluate ranging from 80 ml to 350 ml output was collected, and was divided into the primary fraction (160 ml–350 ml output) and the secondary fraction (80 ml–150 ml output). The primary fraction contained L-arginine, as the major component, the removal efficiency of lysine sodium salt, ornithine sodium salt, citrulline sodium salt, histidine sodium salt, sodium chloride and sodium sulfate being 99%, 98%, 98%, 97% and 99%, respectively. The L-arginine recovery rate was 100%. The color value of the original L-arginine solution was 1.42 (as measured with a spectrophotometer at 400 nm), while that of the primary fraction was 0.024 on average, the degree of decolorization being 92%.

Example 10

Forty milliliters of an aqueous solution containing 61.5 g/l L-glutamine and 7 g/l ammonium L-glutamate were added to the top of a column ($\phi$3.2 cm×H25 cm) packed with 200 ml of $NH_4$-type SK-104S, and water was then introduced at 45° C., at a pH of 5.65 and at an SV of 1.0 to effect elution.

Ammonium L-glutamate was first eluted, followed by elution of L-glutamine. The part of the eluate ranging from 70 ml to 310 ml output was collected, and was divided into the primary fraction (170 ml–310 ml output) and the secondary fraction (70 ml–160 ml output).

The primary fraction contained only L-glutamine, the removal efficiency for ammonium L-glutamate and the L-glutamine recovery rate being both 100%.

Example 11

Forty milliliters of an aqueous solution containing 56 g/l L-glutamine, 0.6 g/l ammonium L-glutamate, 0.9 g/l PCA ammonium salt and 0.4 g/l ammonium sulfate, obtained by dissolving in water crude crystals of L-glutamine recovered from L-glutamine fermentation liquor, were added to the top of a column ($\phi$3.2 cm×H25 cm) packed with 200 ml of $NH_4$-type XFS-XL, and water was then introduced at 45° C. at a pH of 5.59 and at an SV of 1.4 to effect elution.

Ammonium L-glutamate, PCA ammonium salt and ammonium sulfate were first eluted, followed by elution of L-glutamine. The part of the eluate ranging from 70 ml to 370 ml output was collected, and was divided into the primary fraction (160 ml–370 ml output) and the secondary fraction (70 ml–150 ml output).

The primary fraction contained only L-glutamine, the removal efficiency for ammonium L-glutamate, PCA ammonium salt and ammonium sulfate being 100%, 100% and 99.4%, respectively, and the L-glutamine recovery rate being 98.2%. Almost all the ammonium L-glutamate, PCA ammonium salt and ammonium sulfate were recovered in the secondary fraction. The color value of the original L-glutamine solution was 0.039 (as measured with a spectrophotometer at 400 nm), while that of the primary fraction was 0.003 on average, the degree of decolorization being 78.0%.

Example 12

Forty milliliters of an aqueous solution containing 19.3 g/l L-glutamine, 1.0 g/l ammonium L-glutamate, 1.5 g/l PCA ammonium salt and 99 g/l ammonium sulfate, obtained by removal of microbial cells from L-glutamine fermentation liquor, were added to the top of a column ($\phi$3.2×H25 cm) packed with 200 ml of $NH_4$-type XFS-XL, and water was then introduced at 45° C. at a pH of 5.70 and at an SV of 1.0 to effect elution.

Ammonium L-glutamate, PCA ammonium salt and ammonium sulfate were first eluted, followed by elution of L-glutamine. The part of the eluate ranging from 90 ml to 350 ml output was collected, and was divided into the primary fraction (160 ml–350 ml output) and the secondary fraction (90 ml–150 ml output).

The removal efficiency in the primary fraction was 84.8%, 86.6% and 93.0% for ammonium L-glutamate, PCA ammonium salt and ammonium sulfate, respectively, and the L-glutamine recovery rate being 97.5%. The color value of the original L-glutamine solution was 0.641 (as measured with a spectrophotometer at 400 nm), while that of the primary fraction was 0.046 on average, the degree of decolorization being 61.5%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for isolating and purifying an amino acid by ion-exclusion chromatography, which comprises:
   (a) introducing an aqueous solution containing an amino acid to be purified, selected from the group consisting of histidine, threonine, valine, arginine, glutamine and isoleucine, into a column having packed therein a strongly acidic exchange resin, wherein said exchange resin is of the same cation type as the predominant cation exiting in the feed solution, and wherein said resin has a crosslinking degree of 4–8%, and
   (b) adding an aqueous solution to the column to pass through impurities originally contained in the aqueous solution containing the amino acid, and then passing through the purified amino acid, and wherein the flow rate of the elution liquid ranges from 0.5 to 4 SV, and wherein the pH of said aqueous solution for elution is adjusted to the isoelectric pH±1 pH unit of the amino acid to be purified, before being introduced into said column, and
   wherein said impurities for isoleucine, threonine, valine and histidine are composed mainly of at least one member selected from the group consisting of acidic amino acids, sulfate ions, chloride ions and pigments, and the same ion as is adsorbed in said resin;
   and wherein said impurities for arginine are composed mainly of at least one member selected from the group consisting of lysine, ornithine, citrulline, histidine, sulfate ions, chloride ions and pigments, and the same ions as is adsorbed in said resin;
   and wherein said impurities for glutamine are composed mainly of at least one member selected from the group consisting of glutamic acid, pyrrolidone, carboxylic acid and sulfate ions, and the same ion as is adsorbed in said resin.

2. The process according to claim 1, wherein the aqueous solution of an amino acid is a fermentation liquor.

3. The process of claim 2, wherein microbial cells have been removed from said fermentation liquor.

4. The process of claim 1, wherein the aqueous solution of an amino acid is a mother liquid of crystallized amino acid.

5. The process of claim 1, wherein said cation exchange resin is selected from the group consisting of Diaion SK-102, SK-104, SK-106, SKIP, SK-104S, SKIBS, UBK-101L, XFS-43279, XFS-43280, XFS-43281, HCR-W2, TG-8500A, C-20, C-25D, ES-26, C-3, S-100, S-109, SP-112, SP-120, IR-116, IR-118, IR-120B, IR-122, IR-124, IR-252, IR-200, and IR-200 CT.

* * * * *